(12) United States Patent
Rauscher et al.

(10) Patent No.: US 8,702,717 B2
(45) Date of Patent: Apr. 22, 2014

(54) GLENOID ALIGNMENT TOOL

(75) Inventors: Markus Rauscher, Steckborn (CH);
Michele Amiri, Winterthur (CH)

(73) Assignee: Zimmer GmbH, Winterthur (CH)

( * ) Notice: Subject to any disclaimer, the term of this patent is extended or adjusted under 35 U.S.C. 154(b) by 394 days.

(21) Appl. No.: 12/846,277

(22) Filed: Jul. 29, 2010

(65) Prior Publication Data

US 2011/0029088 A1  Feb. 3, 2011

Related U.S. Application Data

(60) Provisional application No. 61/230,259, filed on Jul. 31, 2009.

(51) Int. Cl.
*A61B 17/90* (2006.01)
(52) U.S. Cl.
USPC ............. 606/96; 606/87; 606/104; 623/19.12
(58) Field of Classification Search
USPC ...................... 606/80, 86 R, 87, 96, 102, 104; 623/19.11–19.14
See application file for complete search history.

(56) References Cited

U.S. PATENT DOCUMENTS

| | | | |
|---|---|---|---|
| 5,030,219 A * | 7/1991 | Matsen et al. ................... 606/53 |
| 5,112,335 A | 5/1992 | Laboureau et al. | |
| 5,437,677 A | 8/1995 | Shearer et al. | |
| 5,584,839 A | 12/1996 | Gieringer | |
| 5,769,856 A | 6/1998 | Dong et al. | |
| 6,673,115 B2 | 1/2004 | Resch et al. | |
| 7,294,133 B2 | 11/2007 | Zink et al. | |
| 2004/0230197 A1* | 11/2004 | Tornier et al. ................... 606/87 |
| 2006/0079963 A1* | 4/2006 | Hansen ....................... 623/19.11 |
| 2007/0173945 A1 | 7/2007 | Wiley et al. | |

FOREIGN PATENT DOCUMENTS

| | | |
|---|---|---|
| EP | 0903127 A2 | 3/1999 |
| WO | WO2011/012317 A1 | 2/2011 |

OTHER PUBLICATIONS

International Preliminary Report on Patentability mailed Jan. 31, 2012 from the International Bureau including the Written Opinion of International Application No. PCT/EP2010/004683.
Zimmer Surgical Technique, Anatomical Shoulder Inverse/Reverse System, From Anatomical to Inverse/Reverse, Zimmer 2008, 97-4223-102-00 1.5ML.
Zimmer Surgical Technique, Bigliani-Flatow The Complete Shoulder Solution Cannulated Instruments, Enhancing Glenoid Placement, Zimmer2005,2008, 97-4301-106-00 .5ML.
"International Application Serial No. PCT/EP2010/004683, International Search Report mailed Dec. 7, 2010", 4 pgs.

* cited by examiner

*Primary Examiner* — Todd Manahan
*Assistant Examiner* — Jessica Weiss
(74) *Attorney, Agent, or Firm* — Schwegman Lundberg & Woessner, P.A.

(57) ABSTRACT

An orthopaedic alignment guide component is provided for preparing a patient's bone socket, such as the glenoid of the patient's scapula, to receive a prosthetic glenoid component. The orthopaedic alignment guide component includes a guide body for inserting a guide pin into the patient's scapula and an inferior referencing arm for referencing an inferior surface of the patient's scapula.

17 Claims, 7 Drawing Sheets

GLENOID ALIGNMENT TOOL

CROSS REFERENCE TO RELATED APPLICATION

This application claims priority from U.S. Provisional Patent Application Ser. No. 61/230,259, entitled "GLENOID ALIGNMENT TOOL," filed Jul. 31, 2009, the disclosure of which is hereby expressly incorporated by reference herein in its entirety.

BACKGROUND

1. Field of the Invention

The present invention relates to the field of orthopaedics. More particularly, the present invention relates to an apparatus and method for preparing a patient's bone socket, such as the glenoid of the patient's scapula, to receive a prosthetic component.

2. Description of the Related Art

A patient's shoulder or glenohumeral joint includes a generally ball-shaped head of the humerus that articulates with the glenoid or socket of the scapula. In a healthy shoulder joint, articular cartilage covers the articular portions of the humeral head and the glenoid to facilitate movement of the shoulder joint. However, due to disease or traumatic injury, for example, the articular cartilage of the shoulder joint may be damaged or degenerated.

Such changes to the shoulder anatomy may necessitate replacement of all or part of the natural shoulder joint with prosthetic shoulder components. For example, the natural humeral head may be replaced with a prosthetic humeral component. Also, the glenoid may be replaced with a prosthetic glenoid component. When glenoid replacement is indicated, the glenoid may be resurfaced and shaped to accept the prosthetic glenoid component. The prosthetic glenoid component generally includes an articular surface that is engaged by the prosthetic humeral component.

Reverse shoulder implant systems have been developed in which the conventional ball-and-socket configuration that replicates the natural shoulder joint is reversed, such that a concave prosthetic humeral component and a convex prosthetic glenoid component are provided. Such reverse shoulder implant systems are thought to provide an increased range of motion for treatment of glenohumeral arthritis associated with irreparable rotator cuff damage, for example, by moving the center of rotation between the prosthetic humeral component and the prosthetic glenoid component as compared to traditional shoulder implant systems.

SUMMARY

The present invention provides an orthopaedic alignment guide component for preparing a patient's bone socket, such as the glenoid of the patient's scapula, to receive a prosthetic glenoid component, and a method for using the same. The orthopaedic alignment guide component includes a guide body for inserting a guide pin into the scapula and an inferior referencing arm for referencing an inferior surface of the patient's scapula.

According to an embodiment of the present invention, an orthopaedic alignment guide component is provided for inserting a guide pin into a glenoid of a patient's scapula, the glenoid having a glenoid surface, the scapula including an anterior surface, a posterior surface, a superior surface, and an inferior surface, the anterior surface of the scapula defining an anterior edge of the glenoid, the posterior surface of the scapula defining a posterior edge of the glenoid, the superior surface of the scapula defining a superior edge of the glenoid, and the inferior surface of the scapula defining an inferior edge of the glenoid. The orthopaedic alignment guide component includes a guide body and a referencing arm. The guide body includes a first surface, a second surface opposite the first surface that is contoured to abut the glenoid surface, an anterior portion, a posterior portion, a superior portion, and an inferior portion, the guide body defining a bore that extends through the guide body from the first surface to the second surface, the bore sized to receive the guide pin along a longitudinal axis. The referencing arm extends from the inferior portion of the guide body to contact the inferior surface of the scapula when the second surface of the guide body abuts the glenoid surface.

According to another embodiment of the present invention, a set of orthopaedic alignment guide components is provided for inserting a guide pin into a glenoid of a patient's scapula. The set includes a first orthopaedic alignment guide component having a first guide body and a first referencing arm and a second orthopaedic alignment guide component having a second guide body and a second referencing arm. The first guide body includes a first superior end and a first inferior end, the first guide body extending a first length from the first superior end to the first inferior end, the first guide body defining a first bore that is sized to receive the guide pin. The first referencing arm extends from the first inferior end of the first guide body, the first referencing arm spaced a first distance from the first bore of the first guide body. The second guide body includes a second superior end and a second inferior end, the second guide body extending a second length from the second superior end to the second inferior end that exceeds the first length of the first guide body, the second guide body defining a second bore that is sized to receive the guide pin. The second referencing arm extends from the second inferior end of the second guide body, the second referencing arm spaced a second distance from the second bore of the second guide body, the second distance substantially equaling the first distance.

According to yet another embodiment of the present invention, a method is provided for inserting a guide pin into a glenoid of a patient's scapula, the glenoid having a glenoid surface, the scapula including an anterior surface, a posterior surface, a superior surface, and an inferior surface, the anterior surface of the scapula defining an anterior edge of the glenoid, the posterior surface of the scapula defining a posterior edge of the glenoid, the superior surface of the scapula defining a superior edge of the glenoid, and the inferior surface of the scapula defining an inferior edge of the glenoid. The method comprising the steps of: providing an orthopaedic alignment guide comprising a guide body and a referencing arm, the guide body defining a bore; positioning the guide body against the glenoid surface while contacting the inferior surface of the scapula with the referencing arm; and inserting the guide pin through the bore of the guide body and into the glenoid surface.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
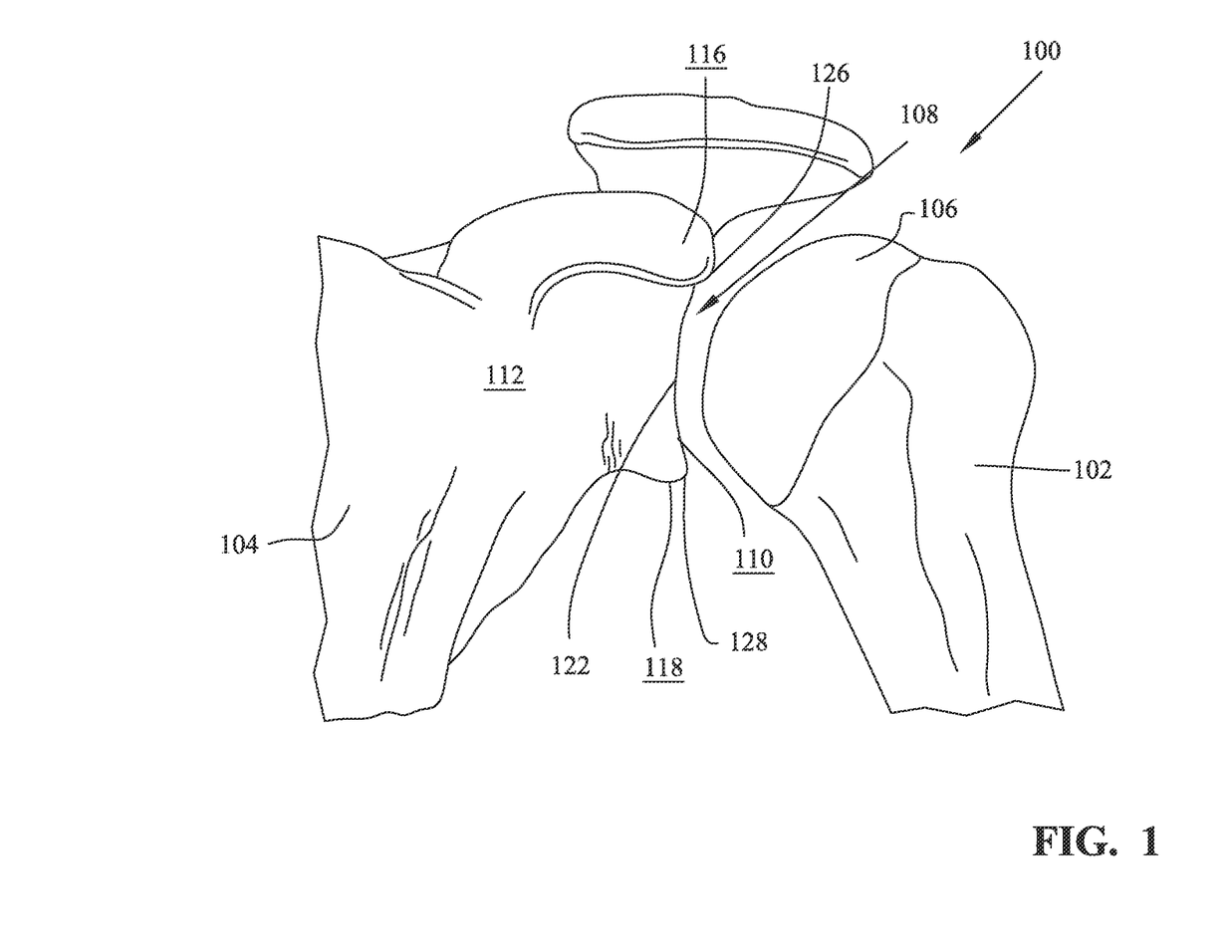
FIG. 1 is an anterior perspective view of a patient's natural shoulder joint, including a humerus and a scapula.
Figure 3:
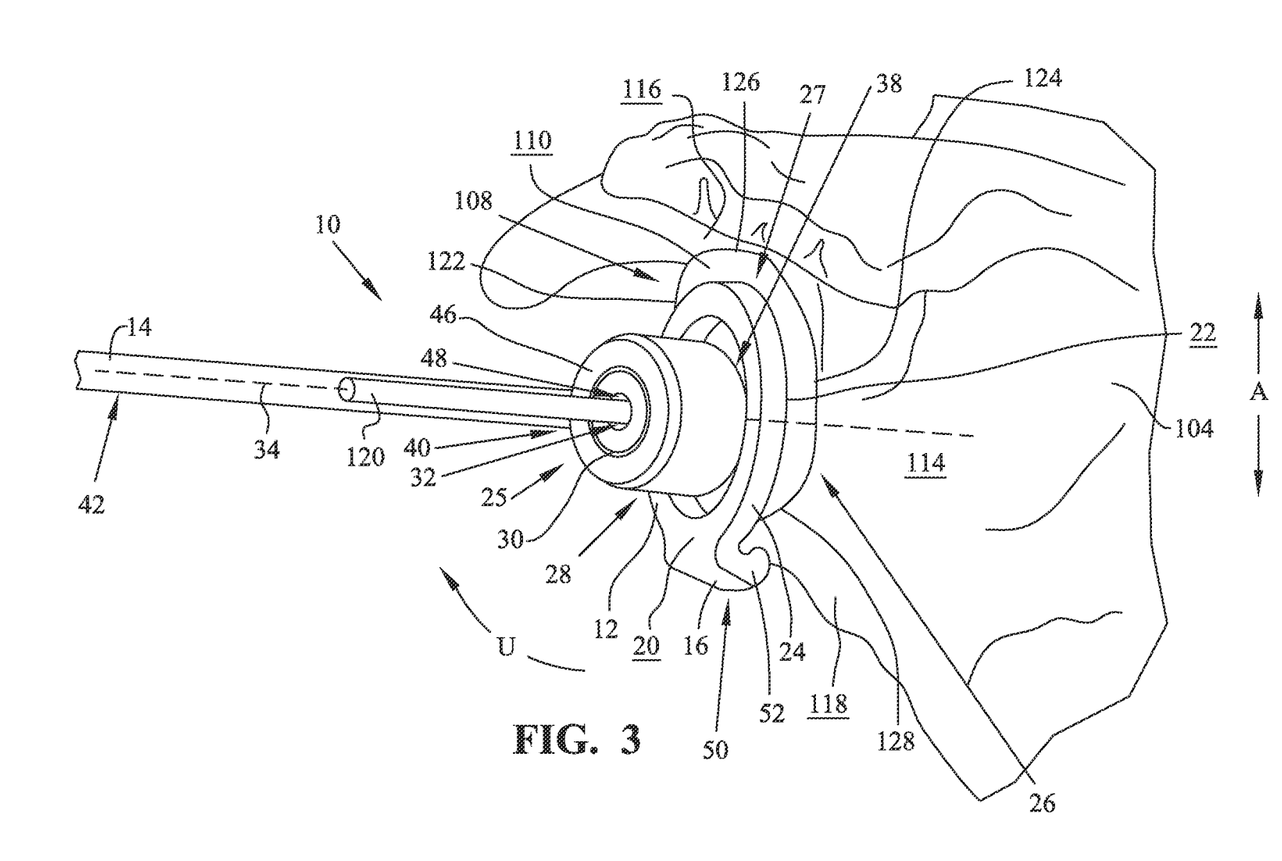
FIG. 3 is a posterior perspective view of the alignment guide component of FIG. 2 mounted onto the scapula of FIG. 1.

A patient's left shoulder joint 100 is illustrated in FIG. 1. The natural shoulder joint 100 includes humerus 102 and scapula 104. Humerus 102 of shoulder joint 100 includes a generally ball-shaped head 106. Scapula 104 of shoulder joint 100 includes glenoid or socket 108 having glenoid surface 110. During movement of the natural shoulder joint 100, head 106 of humerus 102 articulates within glenoid 108 of scapula 104 against glenoid surface 110. As shown in FIGS. 1 and 3, glenoid 108 of scapula 104 is bordered by anterior surface 112, posterior surface 114, superior surface 116, and inferior surface 118 of scapula 104 such that anterior surface 112 of scapula 104 defines anterior edge 122 of glenoid 108, posterior surface 114 of scapula 104 defines posterior edge 124 of glenoid 108, superior surface 116 of scapula 104 defines superior edge 126 of glenoid 108, and inferior surface 118 of scapula 104 defines inferior edge 128 of glenoid 108.

Figure 4:
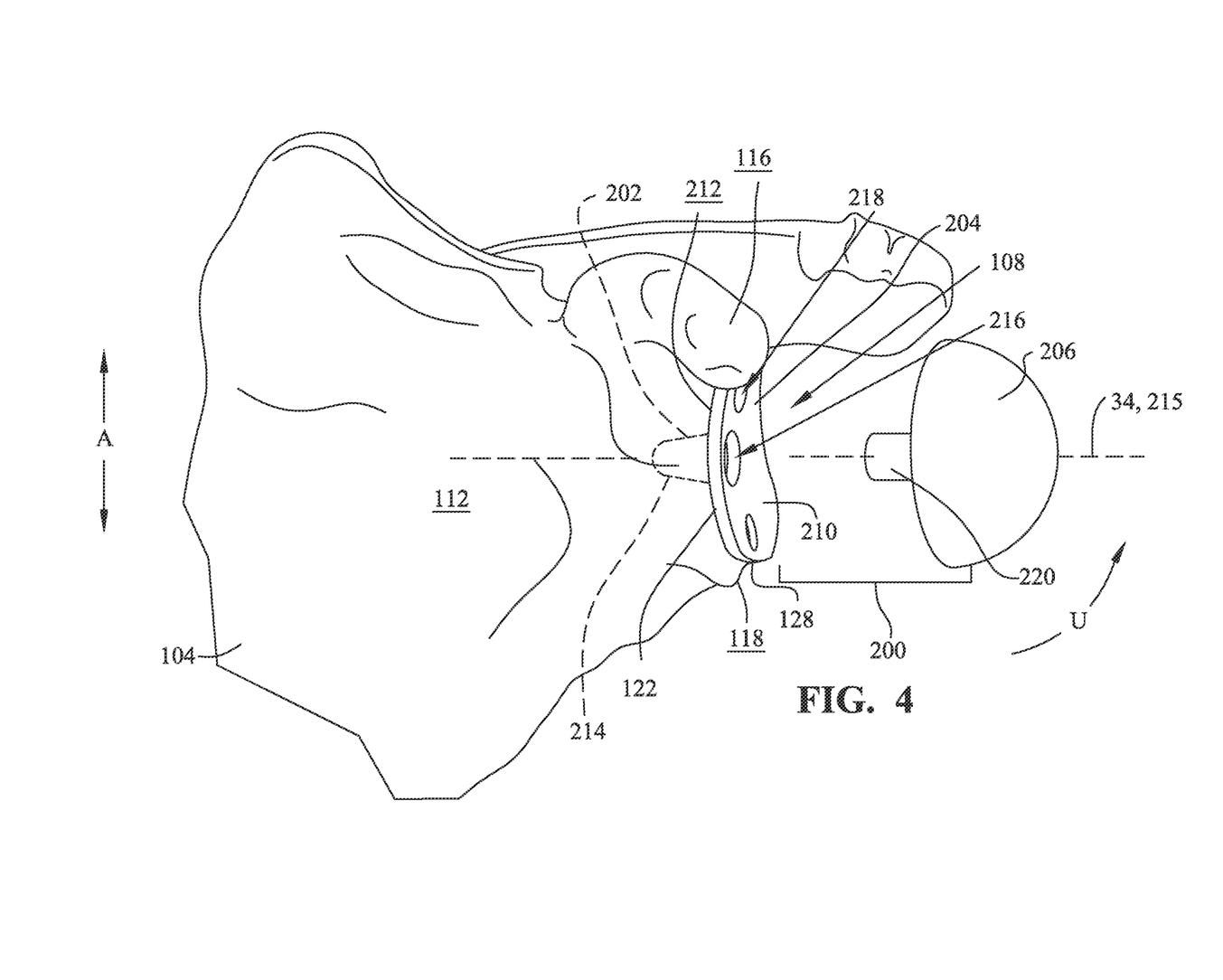
FIG. 4 is an exploded anterior perspective view of a reverse prosthetic glenoid component being implanted into the scapula of FIG. 1, the reverse prosthetic glenoid component including a mounting plate and a prosthetic head.

If scapula 104 of the natural shoulder joint 100 suffers traumatic injury or degenerative changes, for example, a surgeon may replace the natural glenoid 108 with prosthetic glenoid component 200, as shown in FIG. 4. An exemplary procedure for preparing scapula 104 to receive prosthetic glenoid component 200 is set forth below.

First, the surgeon exposes glenoid surface 110 of the natural shoulder joint 100. This step involves making an incision into the patient's skin and moving shoulder muscles away from glenoid surface 110. This step may be performed as set forth in U.S. Pat. No. 7,294,133, entitled "Method and Apparatus for Preparing a Glenoid Surface," filed Jun. 2, 2005, the disclosure of which is hereby expressly incorporated by reference herein.

Next, the surgeon positions alignment guide component 10 against glenoid surface 110, as shown in FIG. 3. An exemplary alignment guide component 10 is illustrated in FIGS. 2 and 3 and includes guide body 12, handle 14, and referencing arm 16.

Figure 2:
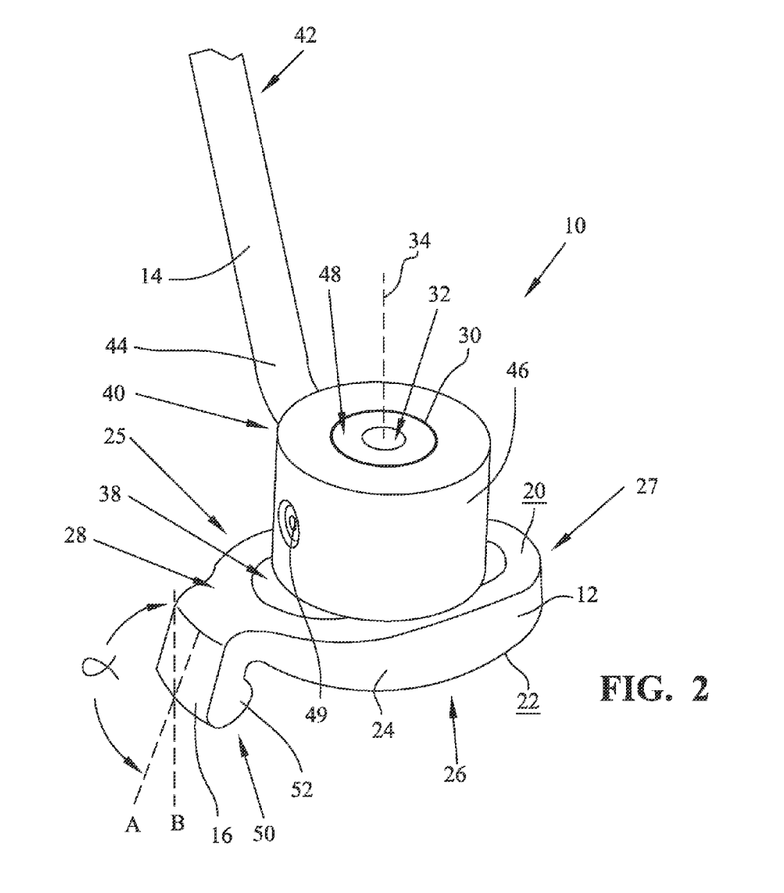
FIG. 2 is a perspective view of an exemplary alignment guide component of the present invention, the alignment guide component including a guide body, a handle, and a referencing arm.

Referring to FIGS. 2 and 3, guide body 12 of alignment guide component 10 includes first surface 20 and a bone-contacting second surface 22 opposite from first surface 20. Second surface 22 of guide body 12 may be slightly convex to match the natural, slightly concave contour of glenoid surface 110. Guide body 12 also includes peripheral wall 24 that joins first surface 20 and second surface 22. Guide body 12 includes first portion 25, second portion 26, superior portion 27, and inferior portion 28. With second surface 22 of guide body 12 resting against glenoid surface 110 of a left shoulder, as shown in FIG. 3, first portion 25 of guide body 12 rests adjacent to anterior surface 112 of scapula 104, second portion 26 of guide body 12 rests adjacent to posterior surface 114 of scapula 104, superior portion 27 of guide body 12 rests adjacent to superior surface 116 of scapula 104, and inferior portion 28 of guide body 12 rests adjacent to inferior surface 118 of scapula 104.

Guide body 12 of alignment guide component 10 further includes a cylindrical guide wall 30 that projects from first surface 20 to define throughbore 32 therein. Throughbore 32 extends entirely through guide body 12 along longitudinal axis 34, from within guide wall 30, to first surface 20, and then to second surface 22 of guide body 12. As discussed further below, guide wall 30 may extend in a direction substantially perpendicular to guide body 12, but throughbore 32 defined within guide wall 30 may or may not also extend in a direction substantially perpendicular to guide body 12. Throughbore 32 of guide body 12 is sized to receive guide pin 120 therein, as described in more detail below. With guide pin 120 inserted into throughbore 32, guide pin 120 also extends along longitudinal axis 34 of throughbore 32.

According to an exemplary embodiment of the present invention, guide body 12 includes at least one viewing aperture 38 that extends entirely through guide body 12 so that the surgeon can view glenoid surface 110 when guide body 12 is proximate glenoid 108. More particularly, the at least one viewing aperture 38 extends from first surface 20 to second surface 22 of guide body 12. As shown in FIGS. 2 and 3, viewing aperture 38 is located radially inwardly of peripheral wall 24.

Referring to FIG. 2, handle 14 of alignment guide component 10 includes first end 40 and second end 42. Between first end 40 and second end 42, handle 14 includes bend 44. First end 40 of handle 14 is configured to couple to guide body 12, and second end 42 of handle 14 is configured to be gripped by a surgeon. From first end 40 to bend 44, handle 14 extends away from first portion 25 of guide body 12 and substantially perpendicularly to longitudinal axis 34 of guide body 12. Then, from bend 44 to second end 42, handle 14 extends upwardly and at an acute angle relative to longitudinal axis 34 of guide body 12. In this embodiment, handle 14 may avoid interfering with humerus 102 (FIG. 1) and surrounding tissue during surgery.

To attach handle 14 to guide body 12, first end 40 of handle 14 includes a cylindrical coupling portion 46 defining chamber 48 therein. Guide wall 30 of guide body 12 is received within chamber 48 of coupling portion 46, such that coupling portion 46 of handle 14 surrounds guide wall 30 of guide body 12. The fact that guide wall 30 of guide body 12 may extend in a direction substantially perpendicular to guide body 12, as discussed above, facilitates application of a normal, balanced force from handle 14 to the central apex (not shown) of bone-contacting second surface 22 of guide body 12 when coupling portion 46 of handle 14 is coupled to guide wall 30 of guide body 12. As shown in FIG. 2, coupling portion 46 of handle 14 may be provided with set screw 49 or another suitable fastener for securing handle 14 to guide body 12. When handle 14 is coupled to guide body 12, throughbore 32 of guide body 12 still remains exposed to receive guide pin 120 (FIG. 3) therein.

According to an exemplary embodiment of the present invention, a desired amount of play may be permitted between guide body 12 and handle 14. For example, guide body 12 may be configured to move about 5 degrees, 10 degrees, or 15 degrees relative to handle 14. In this embodiment, the surgeon may make fine adjustments to the position of guide body 12 to ensure a close, conforming fit between guide body 12 and glenoid surface 110 without having to move handle 14. To achieve a desired amount of play between the components, chamber 48 of coupling portion 46 of handle 14 may be slightly larger than guide wall 30 of guide body 12 and coupling portion 46 of handle 14 may be spaced apart slightly from first surface 20 of guide body 12, thereby permitting coupling portion 46 of handle 14 to tilt relative to guide wall 30 of guide body 12.

According to another exemplary embodiment of the present invention, handle 14 is rotatably coupled to guide body 12 to facilitate use of the same alignment guide component 10 when operating on either a patient's left or right shoulder. In both cases, the surgeon may want handle 14 to project anteriorly from guide body 12. With alignment guide component 10 positioned against glenoid surface 110 of a patient's left shoulder, as shown in FIG. 3, handle 14 extends anteriorly from first portion 25 of guide body 12. If alignment guide component 10 is then moved to a patient's right shoulder, the surgeon may rotate handle 14 by 180 degrees about longitudinal axis 34 until handle 14 extends anteriorly from second portion 26 of guide body 12. Depending upon the particular surgical technique, it is also within the scope of the present invention that the surgeon may want handle 14 to project in any direction, i.e., anteriorly, posteriorly, superiorly, inferiorly, or any combination thereof, from guide body 12.

Referring to FIGS. 2 and 3, referencing arm 16 of alignment guide component 10 protrudes outwardly from guide body 12. More particularly, referencing arm 16 protrudes outwardly from inferior portion 28 of guide body 12. As shown in FIG. 2, referencing arm 16 projects beyond second surface 22 of guide body 12 at an obtuse angle α relative to longitudinal axis 34 of guide body 12. Angle α is defined between line A which extends through referencing arm 16 and line B which extends in a direction perpendicular to guide body 12 (which may be parallel to longitudinal axis 34). At its free end 50, referencing arm 16 includes a flange or protrusion 52.

In operation, and as shown in FIG. 3, the surgeon positions second surface 22 of guide body 12 against glenoid surface 110 with referencing arm 16 protruding inferiorly from inferior portion 28 of guide body 12 and wrapping medially around inferior edge 128 of glenoid 108 toward inferior surface 118 of scapula 104. According to an exemplary embodiment of the present invention, referencing arm 16 bisects inferior edge 128 of glenoid 108. Stated in another way, if glenoid surface 110 is a clock face with the superior-most point of glenoid 108 being 12 o'clock, the inferior-most point of glenoid 108 being 6 o'clock, and the anterior/posterior-most points of glenoid 108 being 3 and 9 o'clock, the surgeon aligns referencing arm 16 with 6 o'clock to bisect inferior edge 128 of glenoid 108. In this embodiment, referencing arm 16 crosses over the inferior-most point of glenoid 108 about halfway between the anterior-most and posterior-most points of glenoid 108.

Then, while maintaining close contact between second surface 22 of guide body 12 and glenoid surface 110, the surgeon moves guide body 12 as necessary in the direction of arrow A to contact inferior surface 118 of scapula 104 with protrusion 52 of referencing arm 16. By referencing inferior surface 118 of scapula 104, the surgeon is able to establish the proper vertical position of guide body 12 along arrow A relative to glenoid 108. More particularly, the surgeon is able to establish the proper vertical position of throughbore 32 along arrow A relative to glenoid 108. Thus, referencing arm 16 of guide body 12 acts as a superior-movement stop or limiting element. Additionally, by referencing inferior surface 118 of scapula 104, the surgeon is able to ensure that longitudinal axis 34 of guide body 12 is properly oriented relative to glenoid 108. For example, by maintaining referencing arm 16 against inferior surface 118 of scapula 104, the surgeon ensures that guide body 12 does not tilt or pivot upwardly or superiorly in the direction of arrow U, which would also cause longitudinal axis 34 of guide body 12 to tilt or pivot upwardly or superiorly along arrow U.

After alignment guide component 10 is properly positioned against glenoid surface 110, the surgeon inserts guide pin 120 into throughbore 32 of guide body 12 and into glenoid surface 110 of glenoid 108, as shown in FIG. 3. Because throughbore 32 of guide body 12 extends along longitudinal axis 34, guide pin 120 also extends along longitudinal axis 34. Guide pin 120 may be a 3 millimeter K-wire, for example, that is coupled to a drill and drilled medially into glenoid surface 110 of glenoid 108. As shown in FIG. 3, guide pin 120 projects laterally beyond glenoid surface 110 and in a direction substantially perpendicular to glenoid surface 110.

Next, the surgeon separates alignment guide component 10 from glenoid surface 110 while leaving guide pin 120 behind to serve as an alignment feature for instruments used to prepare glenoid surface 110. For example, guide pin 120 may serve as an alignment feature for a cannulated reamer (not shown) and/or a drill guide (not shown). Also, guide pin 120 may serve as an alignment feature for a cannulated drill bit (not shown) to drill hole 202 into glenoid 108 around guide pin 120, as shown in FIG. 4. In this embodiment, hole 202 of glenoid 108 also extends along longitudinal axis 34.

After guide pin 120 is no longer needed, the surgeon removes guide pin 120 from glenoid 108. If hole 202 was not previously drilled into glenoid 108 with guide pin 120 in place, the surgeon may now drill or chisel into the hole left behind by guide pin 120 to form an adequately sized hole 202.

Finally, the surgeon implants prosthetic glenoid component 200 into the prepared glenoid 108. As shown in FIG. 4, prosthetic glenoid component 200 is part of a reverse shoulder implant system and includes mounting plate 204 and a generally ball-shaped prosthetic head 206. In this embodiment, prosthetic head 206 of prosthetic glenoid component 200 is configured to articulate with a concave prosthetic humeral component (not shown). An exemplary reverse shoulder implant system is described in U.S. Patent Publication No. 2007/0173945, entitled "Shoulder Arthroplasty System," filed Jan. 18, 2007, the disclosure of which is hereby expressly incorporated by reference herein.

Referring still to FIG. 4, mounting plate 204 of prosthetic glenoid component 200 includes mating surface 210 and a bone-contacting undersurface 212 that achieves intimate contact with the prepared glenoid surface 110. Peg 214 extends from bone-contacting undersurface 212 of mounting plate 204 along longitudinal axis 215 and is sized for receipt within the previously drilled hole 202 in glenoid 108. Peg 214 is at least partially hollow and defines bore 216 therein. Mounting plate 204 also defines multiple screw holes 218.

Prosthetic head 206 of prosthetic glenoid component 200 includes protrusion 220, as shown in FIG. 4. Protrusion 220 of prosthetic head 206 extends toward mounting plate 204 along longitudinal axis 215 and is sized for receipt within bore 216 of peg 214, which also extends along longitudinal axis 215.

According to an exemplary embodiment of the present invention, longitudinal axis 34 of hole 202 in glenoid 108 is substantially the same as longitudinal axis 215 of peg 214 and protrusion 220.

In operation, the surgeon first attaches mounting plate 204 to the prepared glenoid 108. For example, the surgeon may anchor mounting plate 204 to the prepared glenoid by drilling bone screws (not shown) through screw holes 218 of mounting plate 204 and into the prepared glenoid 108. Also, the surgeon inserts peg 214 of mounting plate 204 into the previously drilled hole 202 in glenoid 108 and may secure peg 214 in place using bone cement or another suitable adhesive, for example. According to an exemplary embodiment of the present invention, bone-contacting undersurface 212 and/or peg 214 of mounting plate 204 may include a porous material to encourage bone growth into mounting plate 204. An example of such a porous material is produced using Trabecular Metal™ technology generally available from Zimmer, Inc., of Warsaw, Ind. Trabecular Metal™ is a trademark of Zimmer, Inc.

Then, the surgeon couples prosthetic head 206 to mating surface 210 of mounting plate 204. As shown in FIG. 4, this step involves inserting protrusion 220 of prosthetic head 206 into bore 216 of peg 214. According to an exemplary embodiment of the present disclosure, protrusion 220 of prosthetic head 206 is a tapered component configured to taper couple within peg 214 of mounting plate 204.

As discussed above, the surgeon is able to establish a proper vertical position and orientation of guide pin 120 with respect to glenoid 108 by referencing alignment guide component 10 against inferior surface 118 of scapula 104, as shown in FIG. 3. Guide pin 120 controls the position and orientation of hole 202 in glenoid 108, which in turn controls the position and orientation of prosthetic glenoid component 200 relative to glenoid 108, as shown in FIG. 4. Thus, by referencing alignment guide component 10 against scapula 104, the surgeon is able to establish the proper position and orientation of prosthetic glenoid component 200 relative to glenoid 108. For example, the surgeon is able to establish the proper vertical position of prosthetic glenoid component 200 along arrow A in glenoid 108. Also, the surgeon is able to establish the proper angle of prosthetic glenoid component 200 with respect to glenoid 108, ensuring that prosthetic glenoid component 200 does not tilt too far upwardly along arrow U.

Figure 5:
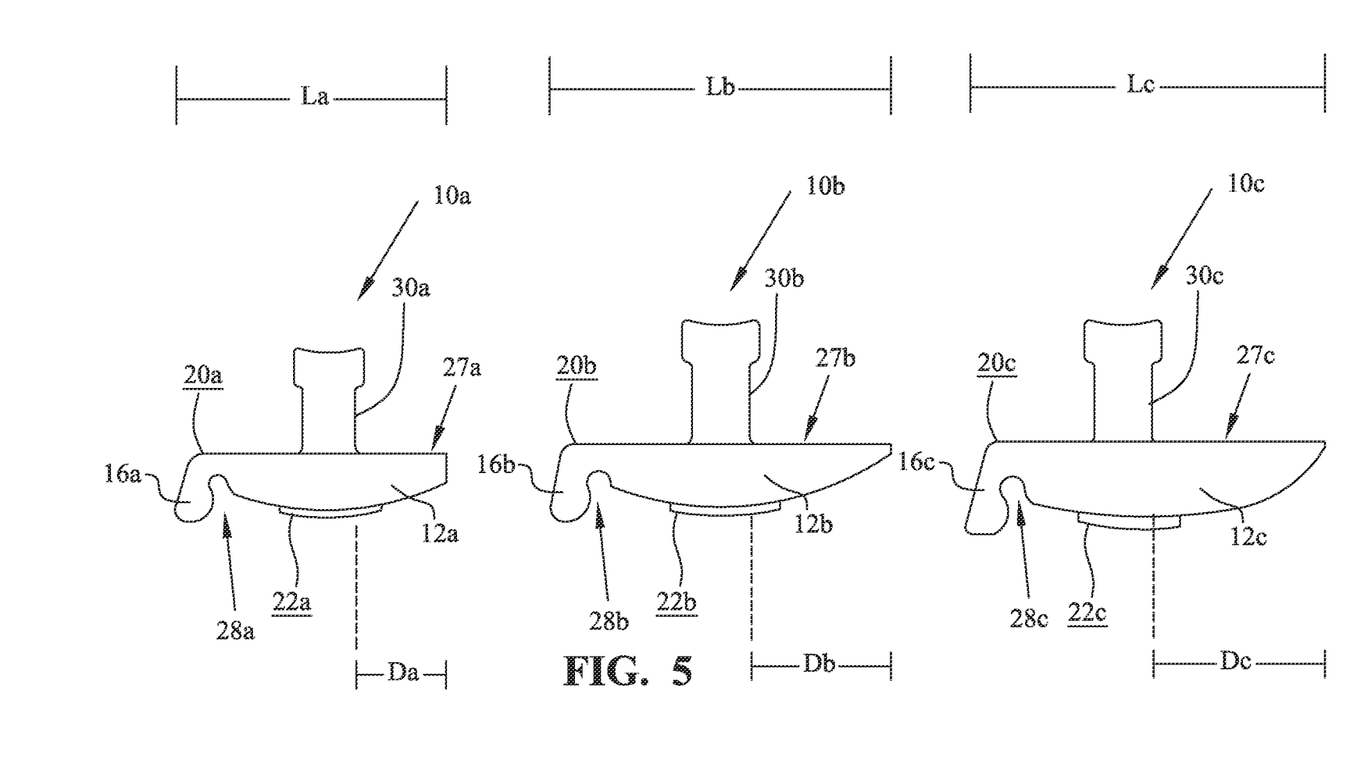
FIG. 5 is an elevational view of an exemplary set of alignment guide components of the present invention, the set including progressively longer guide bodies.
Figure 6:
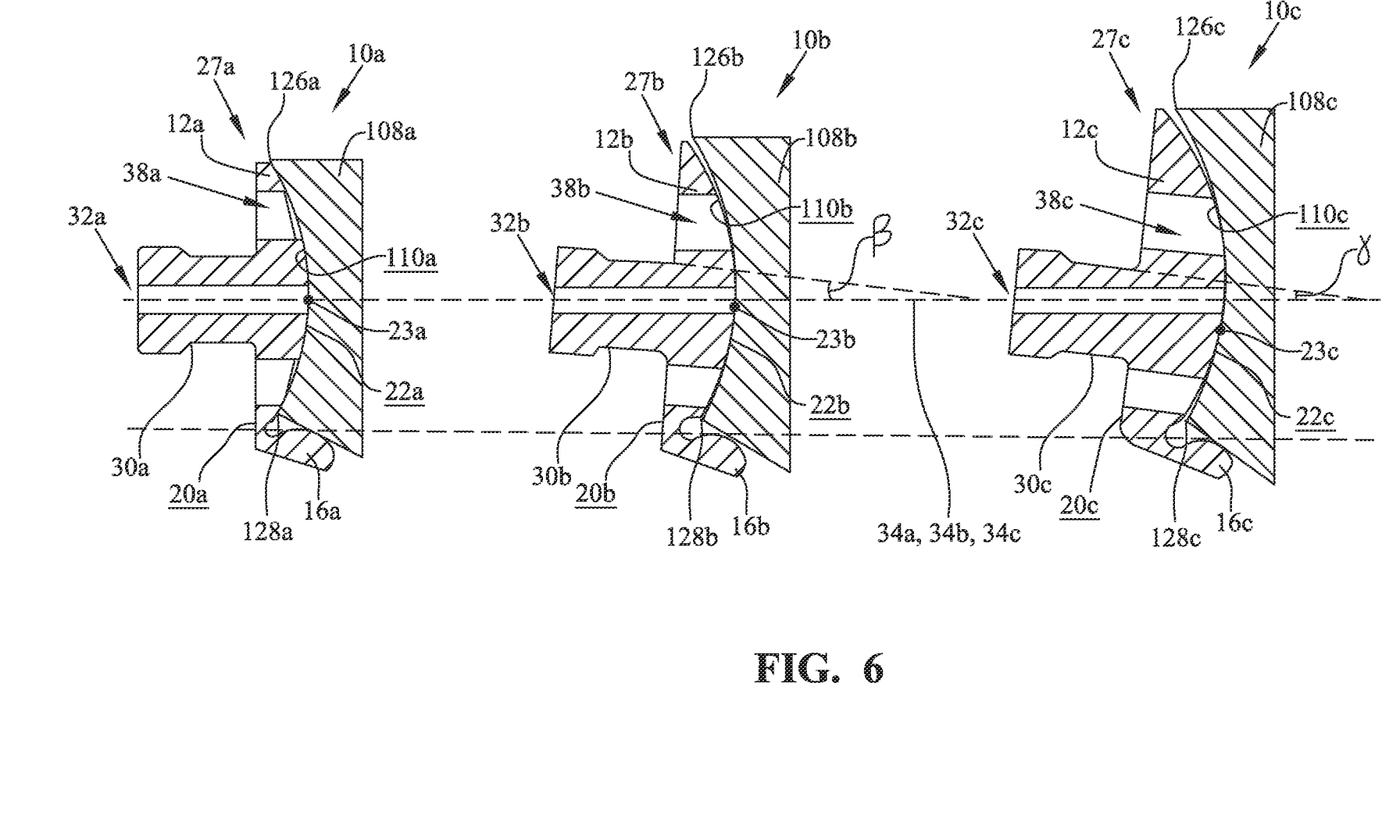
FIG. 6 is a cross-sectional view of the guide bodies of FIG. 5 mounted onto three different scapulas having progressively larger glenoids.

Referring next to FIGS. 5 and 6, a plurality of alignment guide components 10a, 10b, 10c, of different sizes may be provided to the surgeon. More particularly, a plurality of progressively longer guide bodies 12a, 12b, 12c, having lengths La, Lb, Lc, may be provided to the surgeon. Although guide bodies 12a, 12b, 12c, may be provided in different sizes, it is within the scope of the present invention that a single handle 14 (FIG. 2) may be configured to attach to each guide body 12a, 12b, 12c, of the set provided.

As shown in FIGS. 5 and 6, superior portions 27a, 27b, 27c, of guide bodies 12a, 12b, 12c, extend progressively further from guide walls 30a, 30b, 30c, such that the distance Dc between superior portion 27c of guide body 12c and guide wall 30c is greater than the distance Db between superior portion 27b of guide body 12b and guide wall 30b, which is greater than the distance Da between superior portion 27a of guide body 12a and guide wall 30a. In operation, the surgeon selects one of the guide bodies 12a, 12b, 12c, that best matches the size of the patient's glenoid 108a, 108b, 108c. For example, the surgeon may select one of the guide bodies 12a, 12b, 12c, that adequately spans glenoid surface 110a, 110b, 110c, without projecting superiorly beyond glenoid surface 110a, 110b, 110c.

Unlike superior portions 27a, 27b, 27c, of guide bodies 12a, 12b, 12c, inferior portions 28a, 28b, 28c, of guide bodies 12a, 12b, 12c, are spaced substantially equal distances from guide walls 30a, 30b, 30c. Also, referencing arms 16a, 16b, 16c, of guide bodies 12a, 12b, 12c, are substantially the same size. As a result, referencing arms 16a, 16b, 16c, are also spaced substantially equal distances from guide walls 30a, 30b, 30c. Therefore, when longitudinal axes 34a, 34b, 34c, of guide bodies 12a, 12b, 12c, are aligned, as shown in FIG. 6, referencing arms 16a, 16b, 16c, of guide bodies 12a, 12b, 12c, will also be aligned.

In operation, the surgeon selects one of the guide bodies 12a, 12b, 12c, and uses the corresponding referencing arm 16a, 16b, 16c, to properly align the selected one of the guide bodies 12a, 12b, 12c, within glenoid 108a, 108b, 108c, as set forth above. The surgeon then inserts guide pin 120 (FIG. 3) into the corresponding throughbore 32a, 32b, 32c, and into glenoid surface 110a, 110b, 110c, of glenoid 108a, 108b, 108c.

With reference to FIG. 6, as the size of each glenoid 108a, 108b, 108c, increases, guide bodies 12a, 12b, 12c, may rest differently therein. For example, guide body 12a rests essentially upright in the small glenoid 108a, while guide bodies 12b, 12c, are angled or tilted within the larger glenoids 108b, 108c. To ensure that guide pin 120 (FIG. 3) is inserted in a direction substantially perpendicular to each glenoid surface 110a, 110b, 110c, throughbores 32a, 32b, 32c, may be angled or tilted within guide bodies 12a, 12b, 12c, as guide bodies 12a, 12b, 12c, increase in length. For example, longitudinal axis 34a of throughbore 32a may be parallel to cylindrical guide wall 30a, longitudinal axis 34b of throughbore 32b may form angle β with cylindrical guide wall 30b, and longitudinal axis 34c of throughbore 32c may form angle γ with cylindrical guide wall 30c that is greater than angle β. According to an exemplary embodiment of the present invention, angle β equals approximately 2 degrees, 3 degrees, or 4 degrees, and angle γ equals approximately 6 degrees, 7 degrees, or 8 degrees, for example. As a result, longitudinal axis 34a of throughbore 32a intersects apex 23a of second surface 22a of guide body 12a, while apexes 23b, 23c, of second surfaces 22b, 22c, of guide bodies 12b, 12c, are offset from longitudinal axes 34b, 34c, of throughbores 32b, 32c.

Figure 7:
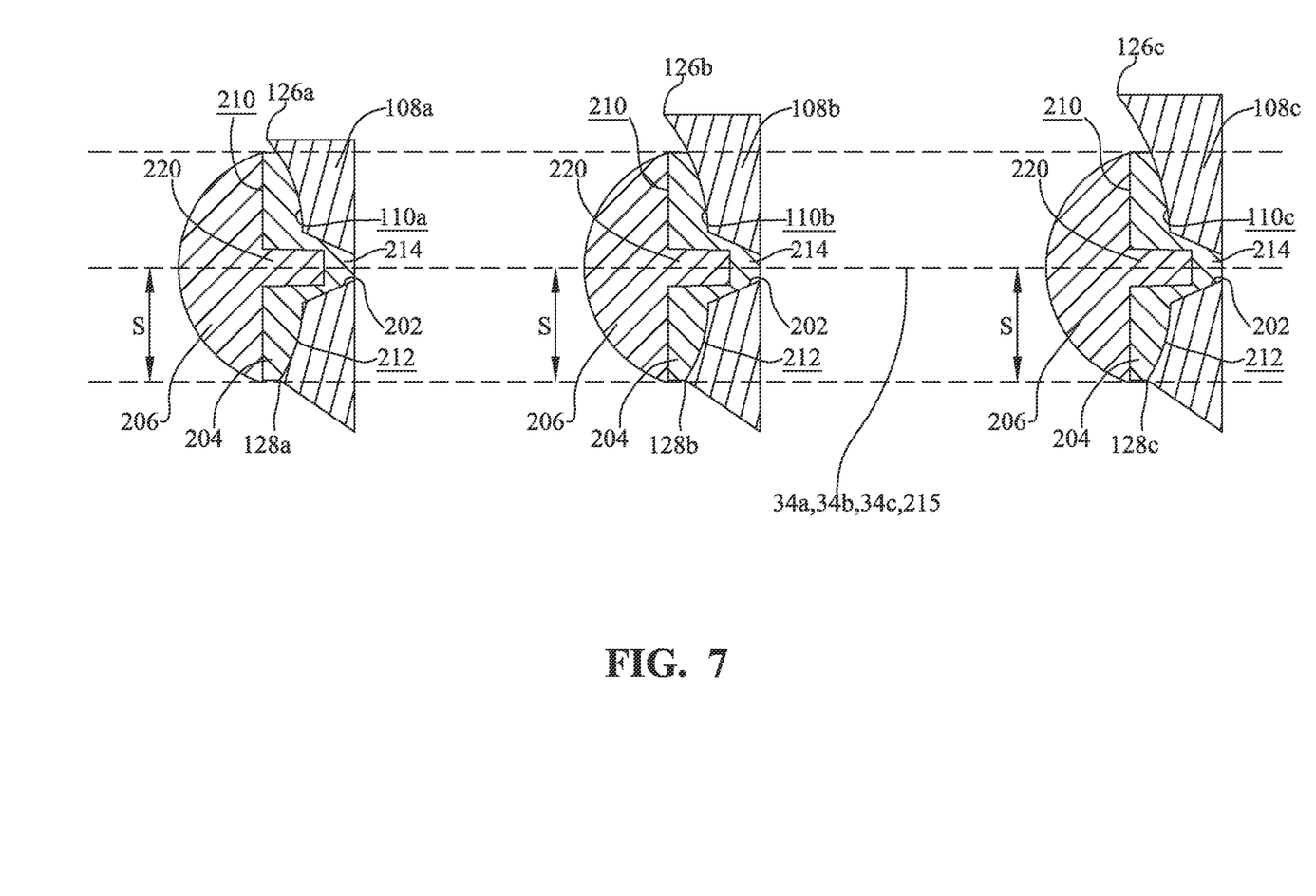
FIG. 7 is a cross-sectional view of the reverse prosthetic glenoid component of FIG. 4 implanted into each of the three different scapulas of FIG. 6.

After guiding guide pin 120 (FIG. 3) in place using the selected guide body 12a, 12b, 12c, the surgeon prepares hole 202 in glenoid 108a, 108b, 108c, in the space once occupied by guide pin 120, as shown in FIG. 7. Like guide pin 120, hole 202 also extends along longitudinal axis 34a, 34b, 34c, of the selected guide body 12a, 12b, 12c. Regardless of the size of the patient's glenoid 108a, 108b, 108c, the surgeon is able to achieve a consistent vertical spacing S between inferior edge 128a, 128b, 128c, of glenoid 108a, 108b, 108c, and hole 202. Also, the surgeon is able to ensure that hole 202 is arranged in a direction substantially perpendicular to glenoid surface 110a, 110b, 110c.

Next, as shown in FIG. 7, the surgeon implants mounting plate 204 and head 206 of prosthetic glenoid component 200 into the prepared glenoid 108a, 108b, 108c. More particularly, the surgeon inserts peg 214 of mounting plate 204 into hole 202 of glenoid 108a, 108b, 108c. As shown in FIG. 7, longitudinal axis 215 of prosthetic glenoid component 200 is substantially the same as longitudinal axis 34a, 34b, 34c, of hole 202. Regardless of the size of the patient's glenoid 108a, 108b, 108c, the surgeon is able to achieve a consistent vertical spacing S between inferior edge 128a, 128b, 128c, of glenoid 108a, 108b, 108c, and peg 214 of mounting plate 204. Also, the surgeon is able to ensure that peg 214 of prosthetic glenoid component 200 extends in a direction substantially perpendicular to glenoid surface 110a, 110b, 110c.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for inserting a guide pin into a glenoid of a patient's scapula, the glenoid having a glenoid surface, the scapula including an anterior surface, a posterior surface, a superior surface, and an inferior surface, the anterior surface of the scapula defining an anterior edge of the glenoid, the posterior surface of the scapula defining a posterior edge of the glenoid, the superior surface of the scapula defining a superior edge of the glenoid, and the inferior surface of the scapula defining an inferior edge of the glenoid, the method comprising the steps of:
    selecting an orthopaedic alignment guide from a set of orthopaedic alignment guides of different sizes, wherein the different sizes of orthopaedic alignment guides in the set can accommodate different glenoid sizes, the set comprising:
    a first orthopaedic alignment guide comprising:
    a first guide body and a first referencing arm, the first guide body defining a first bore that is sized to receive the guide pin, wherein the first guide body includes a first convex bone-contacting surface with a first apex; and
    a second orthopaedic alignment guide comprising:
    a second guide body and a second referencing arm, the second guide body defining a second bore that is sized to receive the guide pin, wherein the second guide body includes a second convex bone-contacting surface with a second apex, the first convex bone-contacting surface having a different curvature than the second convex bone-contacting surface, wherein the first bore has a first longitudinal axis and the second bore has a second longitudinal axis, with the first longitudinal axis being offset from the first apex and/or the second longitudinal axis being offset from the second apex;
    maneuvering the selected orthopaedic alignment guide such that the guide body of the selected orthopaedic alignment guide is positioned against the glenoid surface with the referencing arm of the selected orthopaedic alignment guide abutting the inferior surface of the scapula; and
    inserting the guide pin through the bore of the guide body of the selected orthopaedic alignment guide and into the glenoid surface to form a hole, wherein despite differences in glenoid sizes which affects which orthopaedic alignment guide is selected from the first orthopaedic alignment guide and the second orthopaedic alignment guide a consistent direction of insertion of the guide pin into the glenoid surface can be maintained and a consistent vertical spacing between the inferior edge of the glenoid and the hole can be maintained during said inserting.

2. The method of claim 1, wherein the first guide body includes a first superior end and a first inferior end and wherein the second guide body includes a second superior end and a second inferior end, the first guide body extending a first length from the first superior end to the first inferior end, and the second guide body extending a second length from the second superior end to the second inferior end that exceeds the first length of the first guide body.

3. The method of claim 1, wherein the inserting step comprises inserting the guide pin in a direction substantially perpendicular to the glenoid surface.

4. The method of claim 1, wherein the inserting step comprises inserting the guide pin at an angle through the guide body.

5. A method for inserting a guide pin into a glenoid of a patient's scapula, the glenoid having a glenoid surface, the scapula including an anterior surface, a posterior surface, a superior surface, and an inferior surface, the anterior surface of the scapula defining an anterior edge of the glenoid, the posterior surface of the scapula defining a posterior edge of the glenoid, the superior surface of the scapula defining a superior edge of the glenoid, and the inferior surface of the scapula defining an inferior edge of the glenoid, the method comprising:
    selecting an orthopaedic alignment guide component from a set of orthopaedic alignment guide components of different sizes, wherein the different sizes of orthopaedic alignment guides in the set can accommodate different glenoid sizes, the set comprising:
    a first orthopaedic alignment guide component comprising:
    a first guide body including a first superior end and a first inferior end, wherein the first guide body includes a first convex bone-contacting surface having a first apex, and wherein the first guide body defines a first bore that is sized to receive the guide pin; and
    a first referencing arm extending from the first inferior end of the first guide body, the first referencing arm spaced a first distance from the first bore of the first guide body; and
    a second orthopaedic alignment guide component comprising:
    a second guide body including a second superior end and a second inferior end, wherein the second guide body includes a second convex bone-contacting surface having a second apex, and wherein the second guide body defines a second bore that is sized to receive the guide pin, the first bore having a first longitudinal axis and the second bore having a second longitudinal axis, with the first longitudinal axis being offset from the first apex and/or the second longitudinal axis being offset from the second apex; and
    a second referencing arm extending from the second inferior end of the second guide body, the second referencing arm spaced a second distance from the second bore of the second guide body, the second distance substantially equaling the first distance;
    maneuvering the selected orthopaedic alignment guide component such that the guide body of the selected orthopaedic alignment guide component is positioned against the glenoid surface with the referencing arm of the selected orthopaedic alignment guide component abutting the inferior surface of the scapula; and
    inserting the guide pin through the bore of the guide body of the selected orthopaedic alignment guide component and into the glenoid surface, wherein despite differences in glenoid sizes which affects which orthopaedic alignment guide component is selected from the first orthopaedic alignment guide component and the second orthopaedic alignment guide component a consistent direction of insertion of the guide pin into the glenoid surface can be maintained during said inserting.

6. The method of claim 5, wherein the first guide body extends a first length from the first superior end to the first inferior end, and wherein the second guide body extends a second length from the second superior end to the second inferior end that exceeds the first length of the first guide body.

7. The method of claim 5, wherein the first longitudinal axis is offset from the first apex and the second longitudinal axis is offset from the second apex.

8. The method of claim 7, further comprising a third orthopaedic alignment guide component that includes a third guide body defining a third bore that is sized to receive the guide pin, wherein the third guide body includes a third convex bone-contacting surface having a third apex, and wherein the third bore has a third longitudinal axis that intersects the third apex.

9. The method of claim 7, wherein the first longitudinal axis is offset from the first apex at an angle between 2 degrees and 4 degrees, and the second longitudinal axis is offset from the second apex at an angle between 6 degrees and 8 degrees.

10. The method of claim 5, wherein the first longitudinal axis is offset from the first apex and the second longitudinal axis intersects the second apex.

11. The method of claim 10, wherein the first longitudinal axis is offset from the first apex at an angle between 2 degrees and 8 degrees.

12. The method of claim 5, wherein the first convex bone-contacting surface has a different curvature than the second convex bone-contacting surface.

13. A method for inserting a guide pin into a glenoid of a patient's scapula, the glenoid having a glenoid surface, the scapula including an anterior surface, a posterior surface, a superior surface, and an inferior surface, the anterior surface of the scapula defining an anterior edge of the glenoid, the posterior surface of the scapula defining a posterior edge of the glenoid, the superior surface of the scapula defining a superior edge of the glenoid, and the inferior surface of the scapula defining an inferior edge of the glenoid, the method comprising:
selecting an orthopaedic alignment guide component from a set of orthopaedic alignment guide components of different sizes, wherein the different sizes of orthopaedic alignment guides in the set can accommodate different glenoid sizes, the set comprising:
a first orthopaedic alignment guide component, comprising:
a first guide body including a first convex surface with a first apex, the first convex surface contoured to abut the glenoid surface, the first guide body defining a first bore that is sized to receive the guide pin along a first longitudinal axis; and
a first referencing arm that extends from an inferior portion of the first guide body to contact the inferior surface of the scapula when the first convex surface of the first guide body abuts the glenoid surface; and
a second orthopaedic alignment guide component, comprising:
a second guide body including a second convex surface with a second apex, the second convex surface contoured to abut the glenoid surface, the second guide body defining a second bore that is sized to receive the guide pin along a second longitudinal axis, wherein the second longitudinal axis is offset from the second apex of the second convex surface and/or wherein the first longitudinal axis is offset from the first apex of the first convex surface; and
a second referencing arm that extends from an inferior portion of the second guide body to contact the inferior surface of the scapula when the second convex surface of the second guide body abuts the glenoid surface;
maneuvering the selected orthopaedic alignment guide component such that the guide body of the selected orthopaedic alignment guide component is positioned against the glenoid surface with the referencing arm of the selected orthopaedic alignment guide component abutting the inferior surface of the scapula; and
inserting the guide pin through the bore of the guide body of the selected orthopaedic alignment guide component and into the glenoid surface to form a hole, wherein despite differences in glenoid sizes which affects which orthopaedic alignment guide component is selected from the first orthopaedic alignment guide component and the second orthopaedic alignment guide component a consistent vertical spacing between the inferior edge of the glenoid and the hole can be maintained and a consistent direction of insertion of the guide pin into the glenoid surface can be maintained during said inserting.

14. The method of claim 13, wherein the first longitudinal axis is offset from the first apex and the second longitudinal axis is offset from the second apex.

15. The method of claim 13, wherein the first longitudinal axis is offset from the first apex and the second longitudinal axis intersects the second apex.

16. The method of claim 13, wherein the first guide body includes a first superior end and a first inferior end and wherein the second guide body includes a second superior end and a second inferior end, the first guide body extending a first length from the first superior end to the first inferior end, and the second guide body extending a second length from the second superior end to the second inferior end that exceeds the first length of the first guide body.

17. The method of claim 13, wherein the first convex surface has a different curvature than the second convex surface.

* * * * *